(12) United States Patent
Lee et al.

(10) Patent No.: US 7,074,206 B2
(45) Date of Patent: Jul. 11, 2006

(54) MEDICAL DEVICE BALLOON

(75) Inventors: Jeong S. Lee, Diamond Bar, CA (US); Timoteo Tomas, Union City, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 223 days.

(21) Appl. No.: 10/613,332

(22) Filed: Jul. 3, 2003

(65) Prior Publication Data

US 2004/0096606 A1 May 20, 2004

Related U.S. Application Data

(63) Continuation of application No. 09/451,902, filed on Dec. 1, 1999, now Pat. No. 6,620,127.

(51) Int. Cl.
*A61M 29/00* (2006.01)
*B29C 47/00* (2006.01)

(52) U.S. Cl. .................. 604/96.01; 606/194; 428/36.9

(58) Field of Classification Search ............ 604/96.01, 604/103.06, 103.07, 103.08, 103.09, 103.11; 428/36.9; 525/166, 179; 606/192, 193, 606/194

See application file for complete search history.

(56) References Cited

U.S. PATENT DOCUMENTS

| 4,331,786 A | 5/1982 | Foy et al. |
|---|---|---|
| 4,332,920 A | 6/1982 | Foy et al. |
| 4,898,591 A | 2/1990 | Jang et al. |
| 5,108,415 A | 4/1992 | Pinchuk et al. |
| 5,306,246 A | 4/1994 | Sahatjian et al. |
| 5,328,468 A | 7/1994 | Kaneko et al. |
| 5,554,120 A | 9/1996 | Chen et al. |
| 5,556,383 A | 9/1996 | Wang et al. |
| 5,797,877 A | 8/1998 | Hamilton et al. |
| 5,830,182 A | 11/1998 | Wang et al. |
| 5,849,846 A | 12/1998 | Chen et al. |
| 5,951,494 A | 9/1999 | Wang et al. |
| 6,146,356 A | 11/2000 | Wang et al. |
| 6,200,290 B1 | 3/2001 | Burgmeier |

FOREIGN PATENT DOCUMENTS

| EP | 0 566 755 B1 | 6/1996 |
|---|---|---|
| EP | 0 878 209 A2 | 11/1998 |
| WO | WO 96/32740 | 11/1996 |
| WO | WO 99/13924 | 3/1999 |

*Primary Examiner*—Michael J. Hayes
*Assistant Examiner*—Mark K Han
(74) *Attorney, Agent, or Firm*—Fulwider Patton LLP

(57) ABSTRACT

A balloon catheter having a balloon formed at least in part of a blend of a first polymeric material having a first Shore durometer hardness, and at least a second polymeric material having a second Shore durometer hardness less than the Shore durometer hardness of the first polymeric material. The balloon of the invention has enhanced softness and flexibility due to the presence of the second polymeric material, and a lower than expected compliance. In a presently preferred embodiment, the balloon is formed of a blend of polymeric materials comprising polyether block amides.

18 Claims, 1 Drawing Sheet

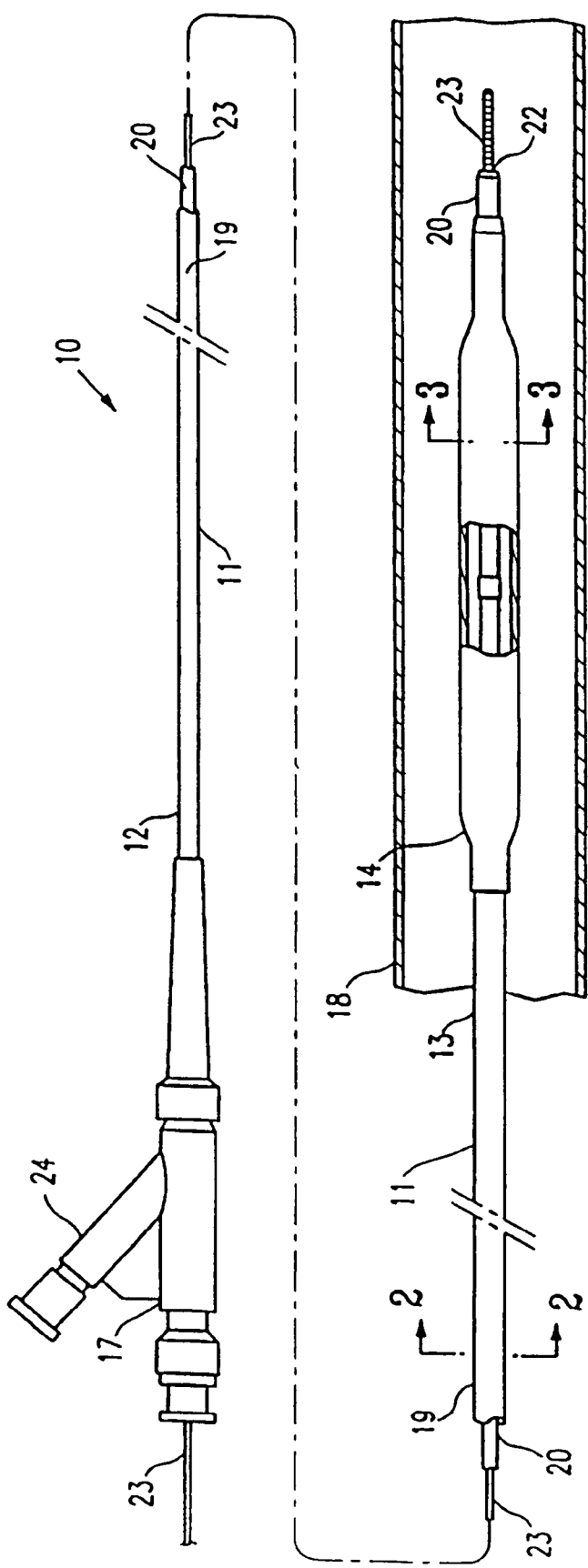
FIG. 1
FIG. 2
FIG. 3

MEDICAL DEVICE BALLOON

This application is a continuation of application Ser. No. 09/451,902. filed Dec. 1, 1999 now U.S. Pat. No. 6,620,127.

BACKGROUND OF THE INVENTION

The invention relates to the field of intravascular catheters, and more particularly to a balloon catheter.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of an dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

In the design of catheter balloons, balloon characteristics such as strength, flexibility and compliance must be tailored to provide optimal performance for a particular application. Angioplasty balloons preferably have high strength for inflation at relatively high pressure, and high flexibility and softness for improved ability to track the tortuous anatomy and cross lesions. The balloon compliance is chosen so that the balloon will have a desired amount of expansion during inflation. Compliant balloons, for example balloons made from materials such as polyethylene, exhibit substantial stretching upon the application of tensile force. Noncompliant balloons, for example balloons made from materials such as PET, exhibit relatively little stretching during inflation, and therefore provide controlled radial growth in response to an increase in inflation pressure within the working pressure range. However, noncompliant balloons generally have relatively low flexibility and softness, so that it has been difficult to provide a low compliant balloon with high flexibility and softness for enhanced trackability.

Therefore, what has been needed is a catheter balloon with relatively low compliance, and with improved ability to track the patient's vasculature and cross lesions therein. The present invention satisfies these and other needs.

SUMMARY OF THE INVENTION

The invention is directed to a balloon catheter having a balloon formed at least in part of a blend of a first polymeric material having a first Shore durometer hardness, and at least one additional polymeric material of essentially the same composition as the first polymeric material but compounded to have a Shore durometer hardness less than the Shore durometer hardness of the first polymeric material. The balloon of the invention has enhanced softness and flexibility due to the presence of the second polymeric material, and a lower than expected compliance. In a presently preferred embodiment, the balloon is formed of a blend of polymeric materials comprising polyether block amides.

In accordance with the invention, the balloon formed from a blend of polymeric materials preferably has a compliance which is not substantially greater than the compliance of a balloon made from 100% of the first polymeric material, e.g. a compliance less than about 20% greater, preferably less than 15% greater, and most preferably less than 10% greater than the compliance of a balloon made from 100% of the higher Shore durometer material. In a preferred embodiment, the compliance of the blend is not greater than the compliance of a balloon formed of 100% of the higher Shore durometer material. Additionally, the polymeric material blend which forms the balloon has a flexural modulus which is less than the flexural modulus of the first polymeric material. The softness and flexibility of a balloon is a function of the flexural modulus of the polymeric material of the balloon, so that a balloon material having a lower Shore durometer hardness, which thus provides a soft and flexible balloon, has a lower flexural modulus. Thus, the balloon of the invention has enhanced softness and flexibility, yet does not have the increased compliance which would be expected from the amount of the second polymeric component having a lower Shore durometer hardness than the first polymeric component.

In one embodiment of the invention, the balloon is semi-compliant or noncompliant. The term "noncompliant", should be understood to mean a balloon with compliance of not greater than about 0.03 millimeters/atmospheres (mm/atm). The term "semi-compliant" should be understood to mean a balloon with a compliance not greater than about 0.045 (mm/atm). In contrast, compliant balloons typically have a compliance of greater than about 0.045 mm/atm.

The first polymeric material may range from about 10 to about 90% of the blend, and the second component of the blend may range from about 90 to about 10%. The blend preferably has an amount of the second polymeric material which is greater than or equal to the amount of the first polymeric material. In a presently preferred embodiment, the balloon is formed of a blend of polyether block amide polymeric materials having different Shore hardness. A suitable polyether block amide copolymer for use in the polymeric blend of the invention is PEBAX, available from Elf Atochem.

The balloon of the invention is formed by extruding a tubular product formed from the blend of the first polymeric component and at least a second polymeric component. In a presently preferred embodiment, the balloon is formed by expanding the extruded tubular product in a balloon mold. Axial tension may be applied to the balloon during expansion, and the balloon may be cooled under pressure and tension between blowing steps. In one embodiment, the balloon is formed by expanding the extruded tubular product in a series of successively larger balloon molds.

Various designs for balloon catheters well known in the art may be used in the catheter system of the invention. For example, conventional over-the-wire balloon catheters for angioplasty or stent delivery usually include a guidewire receiving lumen extending the length of the catheter shaft from a guidewire port in the proximal end of the shaft. Rapid exchange balloon catheters for similar procedures generally include a short guidewire lumen extending to the distal end of the shaft from a guidewire port located distal to the proximal end of the shaft.

The balloon catheter of the invention has improved performance due to the flexibility, softness, and controlled expansion of the balloon. The polymeric blend provides the surprising result of a balloon having relatively low compliance, for controlled balloon expansion, and having relatively high flexibility and softness, for excellent ability to track the patient's vasculature and cross lesions. These and other advantages of the invention will become more apparent from the following detailed description of the invention and the accompanying exemplary drawings.

BRIEF DESCRIPTION OF THE DRAWINGS

FIG. 1 is an elevational view partially in section of a balloon catheter which embodies features of the invention, showing the balloon in an unexpanded state.

FIG. 2 is a transverse cross sectional view of the balloon catheter of FIG. 1 taken along lines 2—2.

FIG. 3 is a transverse cross sectional view of the balloon catheter of FIG. 1 taken along lines 3—3.

DETAILED DESCRIPTION OF THE INVENTION

FIG. 1 illustrates a balloon catheter which embodies features of the invention. The catheter 10 of the invention generally comprises an elongated catheter shaft 11 having a proximal section, 12 a distal section 13, an inflatable balloon 14 formed of a blend of polymeric materials on the distal section 13 of the catheter shaft 11, and an adapter 17 mounted on the proximal section 12 of shaft 11. In FIG. 1, the catheter 10 is illustrated within a patient's body lumen 18, prior to expansion of the balloon 14.

In the embodiment illustrated in FIG. 1, the catheter shaft 11 has an outer tubular member 19 and an inner tubular member 20 disposed within the outer tubular member and defining, with the outer tubular member, inflation lumen 21. Inflation lumen 21 is in fluid communication with the interior chamber 15 of the inflatable balloon 14. The inner tubular member 20 has an inner lumen 22 extending therein which is configured to slidably receive a guidewire 23 suitable for advancement through a patient's coronary arteries. The distal extremity of the inflatable balloon 14 is sealingly secured to the distal extremity of the inner tubular member 20 and the proximal extremity of the balloon is sealingly secured to the distal extremity of the outer tubular member 19.

FIG. 2, showing a transverse cross section of the catheter shaft 11, illustrates the guidewire receiving lumen 22 and inflation lumen 21. The balloon 14 can be inflated by radiopaque fluid introduced at the port in the side arm 24 into inflation lumen 21 contained in the catheter shaft 11, or by other means, such as from a passageway formed between the outside of the catheter shaft and the member forming the balloon, depending on the particular design of the catheter. The details and mechanics of balloon inflation vary according to the specific design of the catheter, and are well known in the art.

Balloon 14 is formed of a blend of polymeric materials, which in a presently preferred embodiment comprises a first polyether block amide polymeric material having a first Shore durometer hardness, and a second polyether block amide polymeric material having a second Shore durometer hardness less than the first Shore durometer hardness. The preferred polymeric material for forming the polymeric blend for the balloon is PEBAX. In one embodiment, the second polymeric material, or the second polyether block amide polymeric material, comprises about 20% to about 80%, preferably about 40% to about 75%, and most preferably about 50% to about 60% by weight of the total weight of the blend of polymeric materials, and the first polymeric material, or the first polyether block amide polymeric material, comprises about 20% to about 80%, preferably about 30% to about 70%, and most preferably about 40% to about 50% by weight of the total weight of the blend of polymeric materials. Most preferably, the amount of the second polymeric material is not less than the amount of the first polymeric material. In a presently preferred embodiment, the first polyether block amide polymeric material has a Shore durometer hardness of about 70D to about 72D, and most preferably about 70D, and the second polyether block amide polymeric material has a Shore durometer hardness of about 55D to about 70D, and most preferably about 63D.

Balloon 14 of the invention preferably has a compliance which is not substantially greater than the compliance of a balloon consisting of the first polyether block amide polymeric material. Balloon 14 has a compliance of about 0.030 mm/atm to about 0.045 mm/atm, and preferably about 0.035, from nominal to the rated burst pressure of the balloon, where the nominal pressure is the pressure required to expand the balloon to its working diameter, and the rated burst pressure, calculated from the average rupture pressure, is the pressure at which 95% of the balloons can be pressurized to without rupturing. For a balloon of the invention, having an outer diatemeter of not greater than 4.0 mm, the nominal pressure is typically about 6 to about 10 atm, and the rated burst pressure is about 14 to about 16 atm. Balloon 14 has a flexural modulus which is less than the flexural modulus of a balloon consisting of the first polyether block amide polymeric material. Balloon 14 has a flexural modulus of about 50,000 to about 100,000 psi, and preferably about 55,000 to about 90,000 psi.

In a presently preferred embodiment, the balloon of the invention is formed by blow molding an extruded tubular product formed of a blend of the first and second polyether block amide polymeric materials. The extruded tubular product is expanded to the final working diameter of the balloon in a balloon mold. The balloon may be heat set in the mold. In one embodiment, the balloon is blown in a series of successively larger balloon molds. Thus, the extruded tubular product is placed in a first mold and the outer diameter of the tubular product is expanded at elevated pressure and temperature to a first outer diameter. The balloon is then placed in a second, larger mold, and expanded at elevated pressure and temperature to a second outer diameter larger than the first outer diameter. The number of successively larger molds used to expand the balloon may vary depending on the balloon material and size. To form a 3.0 mm outer diameter (OD) balloon, the tubular member is expanded in a first mold to an OD of about 2.0 to about 2.5 mm, and then expanded in a second mold to the working diameter of 3.0 mm. Preferably, axial tension is applied to the balloon during expansion, and the balloon is cooled in the mold, under pressure and tension, between blowing steps. However, the balloon of the invention is preferably produced by conventional techniques for producing catheter inflatable members in which the extruded tubular product is expanded in a single mold to the working diameter.

The balloon 14 has sufficient strength to withstand the inflation pressures needed to inflate the balloon. Balloon 14 formed from a blend of the invention preferably has a burst pressure which is not substantially less than the burst pressure of a balloon made from 100% of the first polymeric material, i.e., a burst pressure not more than about 15% to about 20% less than, preferably not more than 5% to about 15% less than the burst pressure of a balloon made from 100% of the first polymeric material. In a preferred embodiment, the burst pressure of balloon 14 is not less than the burst pressure of a balloon formed of 100% of the first polymeric material. The average burst pressure of balloon 14, having an outer diameter of about 3.0 mm, a length of about 20 mm and a dual wall thickness of about 0.036 mm is about 18 atm to about 26 atm. This compares well with the average burst pressure of 18 atm to 26 atm for 3.0 mm balloons blown from 100% of the first polymeric material. The tensile strength of an American Standard Testing Method (ASTM) "dog-bone" sample cut from a compression molded sheet of material is about 8,000 psi to about 9,000 psi. The hoop strength, e.g. the product of the burst pressure and the balloon diameter, divided by two times the balloon wall thickness, of a 3.0 mm balloon of the invention is about 22,000 psi to about 32,000 psi.

The catheter shaft will generally have the dimensions of conventional dilatation or stent deploying catheters. The length of the catheter 10 may be about 90 cm to about 150 cm, and is typically about 135 cm. The outer tubular member 19 has a length of about 25 cm to about 40 cm, an outer diameter (OD) of about 0.039 in to about 0.042 in, and an inner diameter (ID) of about 0.032 in. The inner tubular member 20 has a length of about 25 cm to about 40 cm, an OD of about 0.024 in and an ID of about 0.018 in. The inner and outer tubular members may taper in the distal section to a smaller OD or ID.

The length of the compliant balloon 14 may be about 1 cm to about 4 cm, preferably about 0.8 cm to about 4.0 cm, and is typically about 2.0 cm. In an expanded state, at nominal pressure of about 8 to about 10 atm, the balloon diameter is generally about 0.06 in (1.5 mm) to about 0.20 in (5.0 mm). and the wall thickness is about 0.0006 in (0.015 mm) to about 0.001 in (0.025 mm), or a dual wall thickness of about 0.025 mm to about 0.056 mm. The burst pressure is typically about 18 to 26 atm, and the rated burst pressure is typically about 14 atm.

In a presently preferred embodiment, the balloon 14 typically forms wings, which may be folded into a low profile configuration (not shown) for introduction into and advancement within the patient's vasculature. When inflating the balloon to dilate a stenosis, the catheter 10 is inserted into a patient's vasculature to the desired location, and inflation fluid is delivered through the inflation lumen 21 to the balloon 14 through the inflation port 24. The semi-compliant or noncompliant balloon 14 expands in a controlled fashion with limited radial expansion, to increase the size of the passageway through the stenosed region. Similarly, the balloon has low axial growth during inflation, to a rated burst pressure of about 14 atm, of about 5 to about 10%. The balloon is then deflated to allow the catheter to be withdrawn. The balloon may be used to deliver a stent (not shown), which may be any of a variety of stent materials and forms designed to be implanted by an expanding member, see for example U.S. Pat. No. 5,514,154 (Lau et al.) and U.S. Pat. No. 5,443,500 (Sigwart), incorporated herein in their entireties by reference.

EXAMPLE 1

Polymeric blends were formed using PEBAX 7033 SA01 and PEBAX 6333 SA01. PEBAX 7033 (hereafter "PEBAX 70D") has a Shore durometer hardness of about 70D, a flexural modulus of 67,000 psi, and tensile strength of 8300 psi. PEBAX 6333 (hereafter PEBAX 63D) has a Shore durometer hardness of about 63D, a flexural modulus of 49,000 psi, and a tensile strength of 8100 psi. PEBAX 70D was blended with PEBAX 63D, where the PEBAX 70D was 40% by weight of the total blend and the PEBAX 63D was 60% by weight of the total blend. The blend was used to prepare 15 samples of balloon tubing having a mean ID of about 0.018 inch (0.46 mm) and a mean OD of about 0.034 inch (0.86 mm), with a blow up ratio of 6.6. The balloon tubing may be necked in a die before expanding the balloon tubing in a mold to form the balloon. A balloon was formed from the balloon tubing by axially stretching the balloon tubing at elevated temperature, and expanding the balloon tubing in a balloon mold while heating the balloon tubing by traversing the length of the mold with a heated air nozzle (at about 360° F. to about 420° F. temperature controller set temperature) at a rate of about 1 mm/sec to about 25 mm/sec, and pressurizing the balloon at about 250 psi to about 450 psi to an OD of 3.0 mm (for a blow up ratio of about 6.6). The balloon was then heat treated in the mold by traversing the length of the mold with a second heated air nozzle, for about 5 to about 30 seconds (at about 220° F. to about 300° F. temperature controller set temperature). The balloon was cooled in the mold. The balloons have an OD of about 3.0 mm, a length of 20 mm, and a mean single wall thickness of about 0.00065 inch (0.017 mm) to about 0.00080 inch (0.02 mm). The mean rupture pressure of the balloons was about 20 atm. Radial (OD) compliance measurements made on the blown balloons show a compliance of about 0.036 mm/atm from a nominal OD of about 3.0 mm at about 8 atm to an outer diameter of about 3.25 mm at about 15 atm. Table 1 lists the average balloon OD for the unruptured balloons, at a given inflation pressure.

TABLE 1

| Inflation Pressure (psi)/(atm) | Average Balloon OD (mm) |
| --- | --- |
| 30/2 | 2.603 |
| 45/3 | 2.759 |
| 60/4 | 2.831 |
| 75/5 | 2.887 |
| 90/6 | 2.933 |
| 105/7 | 2.971 |
| 120/8 | 3.004 |
| 135/9 | 3.038 |
| 150/10 | 3.070 |
| 165/11 | 3.102 |
| 180/12 | 3.132 |
| 195/13 | 3.166 |
| 210/14 | 3.202 |
| 225/15 | 3.235 |

TABLE 1-continued

| Inflation Pressure (psi)/(atm) | Average Balloon OD (mm) |
|---|---|
| 240/16 | 3.273 |
| 255/17 | 3.315 |
| 270/18 | 3.350 |
| 285/19 | 3.397 |
| 300/20 | 3.454 |

EXAMPLE 2

PEBAX 70D was blended with PEBAX 63D, where the PEBAX 70D was 40% by weight of the total blend and the PEBAX 63D was 60% by weight of the total blend. The blend was used to prepare balloon tubing having an ID of about 0.0195 inch (0.495 mm) and an OD of about 0.0355 inch (0.902 mm), which was used to prepare balloons having a single wall thickness of about 0.00065 (0.017 mm) to about 0.0008 inch (0.02 mm), with a blow up ratio of about 6.0, using a procedure similar to the procedure outlined in Example 1, except that the same heated air nozzle that was used to heat the balloon tubing during the expansion of the balloon tubing in the mold was used to heat treat the entire length of the balloon within the mold after the balloon tubing is expanded in the mold. Similarly, a second balloon was formed from 100% PEBAX 70D.

Radial (OD) compliance and rupture pressure measurement were made on blown balloons, as listed below in Table 2. The compliance was measured from 8 atm (nominal OD of 3.0) to 14 atm (OD of about 3.25 mm). The balloons formed from a blend of PEBAX 70D and PEBAX 63D had compliance equal to the balloon formed from 100% PEBAX 70D.

TABLE 2

|  | PEBAX 70D 100% | PEBAX 70D/63D 40%/60% |
|---|---|---|
| COMPLIANCE (mm/atm) n = 15 | 0.042 | 0.042 |
| MEAN RUPTURE PRESSURE (psi) n = 15 | 294 | 294 |

EXAMPLE 3

A first balloon was formed from a blend of 60 weight % PEBAX 70D and 40 weight % PEBAX 63D. The blend was used to prepare balloon tubing having an ID of about 0.019 inch (0.495 mm) and an OD of about 0.0355 inch (0.902 mm), and a balloon was formed from the balloon tubing by axially stretching and expanding the balloon tubing in a first mold at 370 psi and 235° C. (temperature controller set temperature) to an OD of 2.0 mm, cooling the balloon in the mold at the elevated pressure, expanding the balloon in a second mold at 370 psi and 237° C. (temperature controller set temperature) to an OD of 3.0 mm and a length of 20 mm, and cooling the balloon in the mold at the elevated pressure. Similarly, a second balloon was formed from a blend of 80 weight % PEBAX 70D and 20 weight % PEBAX 63D, and a third balloon was formed from 100% PEBAX 63D.

Radial (OD) compliance and rupture pressure measurement were made on blown balloons, as listed below in Table 3. The compliance was measured from a nominal pressure required to expand to an OD of about 3.0 (typically about 6–8 atm) to the pressure required to expand the balloon to an OD of approximately 3.25 mm (typically about 11–16 atm). The balloons formed from a blend of 60 weight % PEBAX 70D and 40 weight % PEBAX 63D, despite the higher weight % of the higher Shore durometer PEBAX polymeric material, had substantially similar rupture pressure and compliance compared to the balloons formed from 80 weight % PEBAX 70D and 20 weight % PEBAX 63D. Specifically, the balloons formed of a 60/40 blend had lower rupture pressure and higher compliance than the balloons formed of a 80/20 blend.

TABLE 3

|  | PEBAX 70D/63D 80%/20% | PEBAX 70D/63D 60%/40% | PEBAX 63D 100% |
|---|---|---|---|
| COMPLIANCE (mm/atm) | 0.0304 | 0.0353 | 0.049 |
| MEAN RUPTURE PRESSURE (psi) n = 10 | 311 | 294 | 260 |
| AXIAL GROWTH (mm) | 1.4 | 1.56 | 1.98 |
| DUAL WALL THICKNESS (mm) | 0.038 | 0.037 | 0.042 |

The compliance data for baloons is given below in Tables 4–6.

TABLE 4

PEBAX 70D/63D:80%/20%

| Inflation Pressure (psi)/(atm) | Average Balloon OD (mm) |
|---|---|
| 30/2 | 2.721 |
| 45/3 | 2.777 |
| 60/4 | 2.834 |
| 75/5 | 2.882 |
| 90/6 | 2.930 |
| 105/7 | 2.965 |
| 120/8 | 2.997 |
| 135/9 | 3.027 |
| 150/10 | 3.056 |
| 165/11 | 3.085 |
| 180/12 | 3.114 |
| 195/13 | 3.147 |
| 210/14 | 3.181 |
| 225/15 | 3.217 |
| 240/16 | 3.256 |
| 255/17 | 3.299 |
| 270/18 | 3.347 |
| 285/19 | 3.403 |
| 300/20 | 3.475 |

TABLE 5

PEBAX 70D/63D:60%/40%

| Inflation Pressure (psi)/(atm) | Average Balloon OD (mm) (n = 10) |
|---|---|
| 30/2 | 2.722 |
| 45/3 | 2.788 |
| 60/4 | 2.849 |
| 75/5 | 2.904 |
| 90/6 | 2.943 |
| 105/7 | 2.982 |
| 120/8 | 3.016 |
| 135/9 | 3.048 |

TABLE 5-continued

PEBAX 70D/63D:60%/40%

| Inflation Pressure (psi)/(atm) | Average Balloon OD (mm) (n = 10) |
|---|---|
| 150/10 | 3.082 |
| 165/11 | 3.114 |
| 180/12 | 3.150 |
| 195/13 | 3.191 |
| 210/14 | 3.228 |
| 225/15 | 3.273 |
| 240/16 | 3.319 |
| 255/17 | 3.372 |
| 270/18 | 3.441 |
| 285/19 | 3.525 |
| 300/20 | 3.628 |

TABLE 6

PEBAX 70D/63D:100% 63D

| Inflation Pressure (psi)/(atm) | Average Balloon OD (mm) (n = 10) |
|---|---|
| 30/2 | 2.784 |
| 45/3 | 2.864 |
| 60/4 | 2.931 |
| 75/5 | 2.982 |
| 90/6 | 3.024 |
| 105/7 | 3.063 |
| 120/8 | 3.102 |
| 135/9 | 3.143 |
| 150/10 | 3.190 |
| 165/11 | 3.242 |
| 180/12 | 3.300 |
| 195/13 | 3.360 |
| 210/14 | 3.415 |
| 225/15 | 3.464 |
| 240/16 | 3.541 |
| 255/17 | 3.639 |
| 270/18 | 3.766 |

EXAMPLE 4

Blends of PEBAX 70D and PEBAX 63D were used to form extruded tubing having an ID of 0.0328 inch and an OD of 0.0568 inch. Flexural modulus measurements were made on the extruded tubing using a three point bend test. The average flexural modulus from a sample of 6 specimens was 15.7 gram/mm for the PEBAX 70D 100% formulation, and was 14.4 gram/mm for the PEBAX 70D/63D 80%/20% formulation, and was 11.5 for the PEBAX 70D/63D 40%/60% formulation. Thus, increasing the weight percent of the lower Shore durometer material (i.e., PEBAX 63D) did increase the flexibility of the extruded tubing.

It will be apparent from the foregoing that, while particular forms of the invention have been illustrated and described, various modifications can be made without departing from the spirit and scope of the invention. For example, while the balloon is discussed primarily in terms of a blend of polyether block amides, it should be understood that other blends which have the desired characteristics outlined above may also be used. Although individual features of embodiments of the invention may be described or shown in some of the drawings and not in others, those skilled in the art will recognize that individual features of one embodiment of the invention can be combined with any or all the features of another embodiment. Other modifications may be made without departing from the scope of the invention.

What is claimed is:

1. A balloon catheter, comprising
   a) a shaft having a proximal end, a distal end, and an inflation lumen extending therein; and
   b) a balloon on the shaft which has an interior in fluid communication with the inflation lumen, and which is formed of a blend of polymeric materials comprising a first polyether block amide polymeric material having a first Shore durometer hardness of about 60D to about 72D and being not more than about 50% by weight of the blend, and a second polyether block a mide polymeric material having a second Shore durometer hardness of about 55D to about 70D and less than the first Shore durometer hardness, and the balloon having a rupture pressure not substantially less than a balloon consisting of the first polyether block amide polymeric material.

2. The balloon catheter of claim 1 wherein the balloon has a compliance which is not substantially greater than a compliance of a balloon consisting of the first polyether block amide polymeric material.

3. The balloon catheter of claim 1 wherein the balloon has a compliance which is not greater than a compliance of a balloon consisting of the first polyether block amide polymeric material.

4. The balloon catheter of claim 1 wherein the blend has a flexural modulus lower than a flexural modulus of the first polyether block amide polymeric material.

5. The balloon catheter of claim 1 wherein the balloon mean rupture pressure is equal to a mean rupture pressure of a balloon consisting of the first polyether block amide polymeric material.

6. The balloon catheter of claim 1 wherein the first polyether block amide polymeric material is about 40% by weight of the blend, and the second polyether block amide polymeric material is about 60% by weight of the blend.

7. The balloon of claim 1 wherein the second polyether block amide polymeric material comprises about 40% to about 60% by weight of the total blend.

8. The catheter balloon of claim 1 wherein the first polyether block amide polymeric material comprises about 40% to about 50% by weight of the total blend.

9. The balloon catheter of claim 1 wherein the first polyether block amide polymeric material has a Shore durometer hardness of about 70D.

10. The balloon catheter of claim 1 wherein the second polyether block amide polymeric material has a Shore durometer hardness of about 63D.

11. The balloon catheter of claim 1 wherein the balloon has a compliance of not greater than about 0.045 mm/atm from a nominal to a rated burst pressure of the balloon.

12. The balloon catheter of claim 1 wherein the balloon has a compliance of about 0.03 mm/atm to about 0.035 mm/atm from a nominal to a rated burst pressure of the balloon.

13. The balloon of claim 1 wherein the balloon has a flexural modulus which is less than a flexural modulus of a balloon consisting of the first polyether block amide polymeric material.

14. The balloon catheter of claim 13 wherein the balloon has a flexural modulus which is about 10% to about 36% less than a flexural modulus of a balloon consisting of the first polyether block amide polymeric material.

15. The balloon catheter of claim 1 wherein the balloon has a dual wall thickness of about 0.025 to about 0.056 mm, and a nominal outer diameter of about 1.5 to about 5.0 mm.

16. The balloon catheter of claim 1 wherein the balloon rupture pressure is not more than about 5% to about 15% less than the burst pressure of the balloon consisting of the first polyether block amide polymeric material.

17. A balloon catheter, comprising
a) an elongated shaft having a proximal end, a distal end, and at least one lumen therein; and
b) a balloon formed at least in part of a blend of
a first polyether block amide polymeric material having a first Shore durometer hardness of about 70D, and being about 40% to about 50% by weight of the total blend; and
a second polyether block amide polymeric material having a second Shore durometer hardness which is less than the Shore durometer hardness first polyether block amide polymeric material and which is about 63D, being about 50% to about 60% by weight of the total blend, and the balloon having a rupture pressure not substantially less than a balloon consisting of the first polyether block amide polymeric material.

18. The balloon catheter of claim 1 wherein the balloon has a compliance of not greater than about 0.045 mm/atm over a pressure range of about 8 atm to about 14 atm.

* * * * *

UNITED STATES PATENT AND TRADEMARK OFFICE
CERTIFICATE OF CORRECTION

PATENT NO. : 7,074,206 B2  Page 1 of 1
APPLICATION NO. : 10/613332
DATED : July 11, 2006
INVENTOR(S) : Jeong S. Lee et al.

It is certified that error appears in the above-identified patent and that said Letters Patent is hereby corrected as shown below:

Column 4,
Line 44, delete "diatemeter" and insert --diameter--.

Column 6,
Lines 31 and 37, delete "nozzel" and insert --nozzle--.

Column 7,
Line 23, delete "nozzel" and insert --nozzle--.

Column 10,
Line 16, delete " a mide" and insert --amide--.

Signed and Sealed this

Fourteenth Day of November, 2006

JON W. DUDAS
*Director of the United States Patent and Trademark Office*